United States Patent
Bartolucci et al.

(10) Patent No.: US 9,872,504 B2
(45) Date of Patent: Jan. 23, 2018

(54) BREAD YEAST STRAINS

(71) Applicant: LESAFFRE ET COMPAGNIE, Paris (FR)

(72) Inventors: Jean-Charles Bartolucci, Saint Andre lez Lille (FR); Didier Colavizza, Roubaix (FR); Melanie Legros, La Chapelle d'Armentieres (FR); Georges Pignede, Marcq-en-Baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 654 days.

(21) Appl. No.: 13/922,634

(22) Filed: Jun. 20, 2013

(65) Prior Publication Data

US 2013/0344197 A1   Dec. 26, 2013

Related U.S. Application Data

(63) Continuation-in-part of application No. PCT/FR2011/052916, filed on Dec. 9, 2011.

(30) Foreign Application Priority Data

Dec. 21, 2010 (FR) ...................... 10 04989

(51) Int. Cl.
*A21D 8/04* (2006.01)
*C12N 15/81* (2006.01)
*C12N 1/18* (2006.01)
*C12N 9/26* (2006.01)

(52) U.S. Cl.
CPC ............... *A21D 8/047* (2013.01); *C12N 1/18* (2013.01); *C12N 9/2408* (2013.01); *C12N 9/2431* (2013.01); *C12N 15/81* (2013.01); *C12Y 302/0102* (2013.01); *C12Y 302/01026* (2013.01)

(58) Field of Classification Search
CPC ................................ A21D 8/047; C12N 15/81
USPC ....... 426/19, 62; 435/6, 18, 24, 34, 254, 255
See application file for complete search history.

(56) References Cited

U.S. PATENT DOCUMENTS 5,741,695 A * 4/1998 Loiez nee Hennette ..................
A21D 8/047
426/62

FOREIGN PATENT DOCUMENTS

EP   0511108 A1   4/2001

OTHER PUBLICATIONS

NPL Gueldener in Nucleic Acid Res. 30:6, e23, 2002.*
Taussig et al. In Nucl. Acids Res. 6: 1944-1954, 1989.*
Annexure I: sequence alighnments of SUC2 gene sequence from Taussig et al. vs Applicants SEQ ID#3.*
Database WPI 1-4.6. Week 199733 14-18.Thomson Scientific. London. GB; Application No. 1997-357898 and JP 9 149785 A (Nippon Ten Sai Seito KK). Jun. 10, 1997 (Jun. 10, 1997).
EMR S.D. et al, "An MF-Alpha-1-SUC-2 Alpha Factor Invertase EC-3.2.1.26 Gene Fusion for Study of Protein Localization and Gene Expression in Yeast *Saccharomyces-cerevisiae*," Proceedings of the National Academy of Sciences of the United States of America, vol. 80. No. 23. 1983. pp. 7080-7084.

* cited by examiner

*Primary Examiner* — Amber R Orlando
*Assistant Examiner* — Bhaskar Mukhopadhyay
(74) *Attorney, Agent, or Firm* — Vedder Price P.C.; Thomas J. Kowalski; Deborah L. Lu

(57) ABSTRACT

The present invention relates to novel broad spectrum strains of baker's yeast, i.e. yeast strains that are effective on both dough known as unsweetened dough and dough known as sweet dough.

7 Claims, No Drawings

SEQUENCE LISTING

<160> NUMBER OF SEQ ID NOS: 3

<210> SEQ ID NO 1
<211> LENGTH: 34
<212> TYPE: DNA
<213> ORGANISM: Bacteriophage P1

<400> SEQUENCE: 1

```
ataacttcgt ataatgtatg ctatacgaag ttat                           34
```

<210> SEQ ID NO 2
<211> LENGTH: 103
<212> TYPE: DNA
<213> ORGANISM: Artificial Sequence
<220> FEATURE:
<223> OTHER INFORMATION: loxP and flanking regions

<400> SEQUENCE: 2

```
tgaagcttcg tacgctgcag gtcgacaacc cttaatataa cttcgtataa tgtatgctat    60
acgaagttat taggtgatat cagatccact agtggcctat gcg                     103
```

<210> SEQ ID NO 3
<211> LENGTH: 1599
<212> TYPE: DNA
<213> ORGANISM: Saccharomyces cerevisiae

<400> SEQUENCE: 3

```
atgcttttgc aagctttcct tttccttttg gctggttttg cagccaaaat atctgcatca    60
atgacaaacg aaactagcga tagacctttg gtccacttca cacccaacaa gggctggatg   120
aatgacccaa atgggttgtg gtacgatgaa aaagatgcca aatggcatct gtactttcaa   180
tacaacccaa atgacaccgt atggggtacg ccattgtttt ggggccatgc tacttccgat   240
gatttgacta attgggaaga tcaacccatt gctatcgctc ccaagcgtaa cgattcaggt   300
gctttctctg gctccatggt ggttgattac aacaacacga gtgggttttt caatgatact   360
attgatccaa gacaaagatg cgttgcgatt tggacttata cactcctga aagtgaagag   420 caatacatta gctattctct tgatggtggt tacacttta ctgaataccaa aaagaaccct   480 gttttagctg ccaactccac tcaattcaga gatccaaagg tgttctggta tgaaccttct   540
caaaaatgga ttatgacggc tgccaaatca caagactaca aaattgaaat ttactcctct   600
gatgacttga agtcctggaa gctagaatct gcatttgcca atgaaggttt cttaggctac   660
caatacgaat gtccaggttt gattgaagtc ccaactgagc aagatccttc caaatcttat   720
tgggtcatgt ttatttctat caacccaggt gcacctgctg gcggttcctt caaccaatat   780
tttgttggat ccttcaatgg tactcatttt gaagcgtttg acaatcaatc tagagtggta   840
```

```
gattttggta aggactacta tgccttgcaa actttcttca acactgaccc aacctacggt    900
tcagcattag gtattgcctg ggcttcaaac tgggagtaca gtgcctttgt cccaactaac    960
ccatggagat catccatgtc tttggtccgc aagttttctt tgaacactga atatcaagct   1020
aatccagaga ctgaattgat caatttgaaa gccgaaccaa tattgaacat tagtaatgct   1080
ggtccctggt ctcgttttgc tactaacaca actctaacta aggccaattc ttacaatgtc   1140
gatttgagca actcgactgg taccctagag tttgagttgg tttacgctgt taacaccaca   1200
caaaccatat ccaaatccgt ctttgccgac ttatcacttt ggttcaaggg tttagaagat   1260
cctgaagaat atttgagaat gggttttgaa gtcagtgctt cttccttctt tttggaccgt   1320
ggtaactcta aggtcaagtt tgtcaaggag aacccatatt tcacaaacag aatgtctgtc   1380
aacaaccaac cattcaagtc tgagaacgac ctaagttact ataaagtgta cggcctactg   1440
gatcaaaaca tcttggaatt gtacttcaac gatggagatg tggtttctac aaatacctac   1500
ttcatgacca ccggtaacgc tctaggatct gtgaacatga ccactggtgt cgataatttg   1560
ttctacattg acaagttcca agtaagggaa gtaaaatag                          1599
```

BREAD YEAST STRAINS

CROSS REFERENCE TO RELATED APPLICATIONS

This application is a continuation-in-part of International Patent Application No. PCT/FR2011/052916 filed Dec. 9, 2011, and published as WO2012/085386, which claims priority from FR 10 04989 filed Dec. 21, 2010. All of the above-mentioned applications, as well as all documents cited herein and documents referenced or cited in the documents cited herein, are hereby incorporated herein in their entirety by reference.

FIELD OF THE INVENTION

The present invention relates to novel broad spectrum strains of baker's yeast, i.e. yeast strains that are effective on both dough known as unsweetened dough and dough known as sweet dough.

BACKGROUND OF THE INVENTION

Document EP 0 511 108 describes broad spectrum yeast strains obtained by a program for crossing strains coupled with selection steps. The haploids and hybrid strains obtained by crossing them are selected on the basis of a high maltopermease activity and high maltase activity in the presence of glucose (and in the absence of maltose) and on the basis of a low invertase activity.

Document JP 9-149785 describes broad spectrum baker's yeast strains obtained by hybridization, wherein one of the haploid parent strains is deficient in invertase. The strains obtained are then selected on the basis of an invertase activity of 10 to 50 units and a maltase activity of at least 40 units, allowing said broad spectrum yeast strains to be obtained. According to that document, one unit of invertase activity corresponds to the formation of one milligram of reducing sugars per gram of yeast in one minute at 67% humidity.

Moreover, document EP 0 511 108 indicates that it is possible to reduce the invertase activity by means of molecular genetics by disrupting one or more SUC genes, preferably in haploids that have a maximum of one or two SUC genes.

The various selection steps, carried out on the basis of several criteria and involving at the same time the parent strains, the haploids and the hybrids, allow the chances of obtaining a broad spectrum yeast strain to be improved. However, the method for obtaining broad spectrum yeast strains as described in document EP 0 511 108 is relatively long and cumbersome in its execution.

Document EP 0 994 192 describes a novel excision cassette for use in yeast. This excision cassette means that no exogenous DNA is left in the yeast.

For example, document EP 0 994 192 describes the disruption of three copies of the SUC gene using, in succession, three excision cassettes each comprising: two recombinogenic sequences flanking two direct repeat sequences (mosaic sequence), themselves flanking a negative selection marker (RTA suicide gene) and a positive selection marker (kanamycin). The mosaic sequence is a non-heterologous DNA sequence from *Saccharomyces cerevisiae* comprising 97 base pairs.

The excision method described in document EP 0 994 192 is useful when disrupting a limited number of genes. However, it is not suitable for disrupting a larger number of genes: the excision method in fact involves constructing as many excision cassettes, and comprises as many disruption steps, as there are genes to be excised. The method described in EP 0 994 192 then becomes much too lengthy and cumbersome to carry out. In addition, the method described in document EP 0 994 192 cannot be used to disrupt more than 4 copies of the SUC gene, given the length of the recombinogenic sequence used and the size of the SUC gene.

The availability of broad spectrum yeast strains is useful to an industrial. In fact, it is then possible to produce, in the same unit and from a single yeast strain, yeasts intended for application to unsweetened dough and yeasts intended for application to sweet dough. Thus, the use of a broad spectrum yeast strain saves time and space in the factory, and therefore improves productivity.

The aim of the present invention is to provide a novel method that is rapid, effective and simple to implement in order to obtain novel broad spectrum baker's yeast strains.

SUMMARY OF THE INVENTION

In a first aspect, the invention provides a broad spectrum strain of *Saccharomyces cerevisiae*, characterized in that:
  n copies of a SUC gene are inactivated, n being a whole number, such that the invertase activity of said strain is 20 units or less; and
  the maltase activity of said strain, before inactivation of the n copies of the SUC gene, is less than 80 units.

In a second aspect, the invention concerns a method for obtaining a broad spectrum strain of *Saccharomyces cerevisiae*, comprising the steps of:
  selecting a strain of *Saccharomyces cerevisiae* having:
    a maltase activity of less than 80 units; and
    a fermentative capacity of 110 mL or more in an unsweetened dough;
  inactivating m copies of a SUC gene of said selected strain, m being a whole number, such that the invertase activity of the selected and inactivated strain is 20 units or less.

In a third aspect, the invention concerns a broad spectrum strain of *Saccharomyces cerevisiae* that is susceptible of being obtained by the method as defined above.

In a fourth aspect of the invention, a yeast strain is provided that is derived from a strain as defined above, characterized in that said derived yeast strain is a broad spectrum strain with an invertase activity of 20 units or less.

In a fifth aspect of the invention, a yeast is provided that is obtained by culture of a yeast strain as defined above or a derived strain as defined above.

In a sixth aspect, the invention concerns the use of a yeast as defined above for the manufacture of bakery products.

In a seventh aspect, the invention concerns the use of a reduction in invertase activity in order to obtain a broad spectrum yeast strain from a yeast strain with a low maltase activity and a fermentative capacity of 110 mL or more in an unsweetened dough.

FREE TEXT OF SEQUENCE LISTING

Sequence SEQ ID No: 2 is an artificial sequence comprising the loxP sequence and the flanking regions ("loxP and flanking regions").

DETAILED DESCRIPTION OF THE INVENTION

Thus, the aim of the present invention is to provide a novel method that is rapid, efficient and simple to implement for obtaining novel broad spectrum baker's yeast strains.

Surprisingly and unexpectedly, the Inventors have demonstrated that it is possible to obtain broad spectrum yeast strains from yeast strains with a low maltase activity.

A broad spectrum yeast strain is a yeast strain that is effective with both unsweetened dough and sweet dough.

"Unsweetened dough" as used herein refers to a dough to which no sugar has been added.

In an unsweetened dough, the sugars that are present come from the flour.

"Sweet dough" as used herein denotes a dough with an added saccharose content of 14% by weight or more with respect to the weight of the flour, preferably 20% or more.

A sweet dough is, for example, a dough with an added sugar content equal to 25% or 26% by weight with respect to the weight of flour.

The performance of a yeast strain can be evaluated by measuring its fermentative capacity.

The fermentative capacity of a yeast strain corresponds to the volume of $CO_2$ (in mL) produced by the yeast during fermentation in flour dough pieces.

In the context of the present invention, the fermentative capacity of a strain is measured after culture of said strain on molasses plate.

The culture of a yeast strain on molasses plate is described in Example 1.

The fermentative capacity is measured using conventional techniques that are known to the skilled person adapted from the protocol described by Burrows and Harrison in the "Journal of the Institute of Brewing", Vol 65, 1959.

The fermentative capacity is in particular measured using a fermentometer or a Risograph (for example National Manufacturing, Lincoln, Nebr.).

The fermentative capacity was measured here on dough pieces constituted by flour and a suspension of yeasts obtained by culture of the strain on molasses plate for a period of 2 hours (cf. Example 1).

The suspension of yeasts is constituted by 150 mg dry yeast matter when measuring the fermentative capacity in an unsweetened dough or 300 mg dry yeast matter when measuring the fermentative capacity in a sweet dough in 15 mL of an aqueous solution of 27 g/L NaCl and 4 g/L of $SO_4(NH_4)_2$.

In order to form the dough pieces, the flour and the suspension of yeasts are mixed for 40 seconds in a kneader in order to obtain a dough. The dough is then placed in a receptacle in a water bath at 30° C. 13 minutes after starting the mixing, the receptacle containing the dough is hermetically sealed and the volume of gas is measured after 2 hours.

Unless otherwise indicated, the fermentative capacity corresponds to the total volume of gas produced, in mL, over a period of 2 hours at 30° C.

In the context of the present invention, the fermentative capacity of a yeast strain in an unsweetened dough is measured in a dough containing 20 g of flour.

In the context of the present invention, the fermentative capacity of a yeast strain in a sweet dough is measured in a dough containing 6.5 g of saccharose and 25 g of flour.

A broad spectrum yeast strain within the meaning of the invention is a yeast strain having:
 a fermentative capacity of 110 mL or more in an unsweetened dough; and
 a fermentative capacity of 90 mL or more in a sweet dough.

A preferred broad spectrum yeast strain is a yeast strain having:
 a fermentative capacity of 120 mL or more, preferably 130 mL or more in an unsweetened dough; and
 a fermentative capacity of 95 mL or more, preferably 100 mL or more in a sweet dough.

Surprisingly and unexpectedly, the Inventors have thus demonstrated that it is possible to endow a yeast strain with a broad spectrum character simply by reducing its invertase activity, despite the fact that said yeast strain has a low maltase activity.

Thus, the present invention concerns broad spectrum yeast strains, characterized in that they have a low invertase activity and in that they are obtained from a yeast strain with a low maltase activity.

The present invention concerns only strains of *Saccharomyces cerevisiae*.

As a consequence, the terms "yeast strain" or "strain of *Saccharomyces cerevisiae*" will be used interchangeably.

The invertase activity is provided by at least one invertase enzyme.

Invertase converts one molecule of saccharose into one molecule of glucose and one molecule of fructose.

A low invertase activity herein denotes an invertase activity of 20 units or less, the invertase activity being measured after culture of the yeast strain on molasses plate (cf. Example 1).

One invertase unit corresponds to 1 µmole of reducing sugar liberated in 5 minutes per mg of dry yeast matter, at 30° C. and at a pH of 4.7, without plasmolysis of the yeast.

The invertase activity can be measured using tests that are well known to the skilled person.

As an example, the invertase activity is measured as follows: a known quantity, of the order of a few tens of milligrams of dry yeast matter and saccharose in a concentration of 0.1 molar, are brought together in a buffered medium (acetate buffer, at 50 mM, and at pH 4.7) and the entirety is placed in a water bath at 30° C. After incubating for 5 minutes, the saccharose inversion reaction is blocked by adding a dinitrosalicylic acid reagent that serves to assay, using a spectrophotometer at a wavelength of 540 nm, the reducing sugars formed by means of a colorimetric reaction.

In a preferred embodiment, a broad spectrum yeast strain in accordance with the invention has an invertase activity of 17 units or less, preferably 15 units or less.

The maltase activity is measured in this case in a condition of repression, i.e. after culture in the presence of glucose and in the absence of maltose.

A low maltase activity denotes herein an activity of less than 80 units, the maltase activity being measured after culture of the yeast strain on a molasses plate, followed by incubation in a medium containing glucose in the absence of maltose (cf. Example 1).

One maltase unit corresponds to 1 nanomole of p-nitrophenol liberated per minute and per mg of proteins.

The maltase activity can be measured using tests that are familiar to the skilled person.

As an example, the maltase activity is measured by assaying the liberation of a colored product, p-nitrophenol, following the action of maltase on a chromogenic substrate, 4-nitrophenyl-α-D-glucopyranoside, as described by Houghton-Larsen and Anders Brandt, Appl Environ Microbiol, 2006, pp 7176-7182.

The maltase activity is measured in this case after culture of the yeast strain on a molasses plate and incubation, in particular for 4 hours, in a medium containing glucose (cf. protocol described in Example 1).

An essential feature of the invention resides in the fact that the broad spectrum yeast strain has a low invertase activity.

The *Saccharomyces cerevisiae* SUC genes family comprises 6 genes coding for invertase (SUC1 to SUC5 and SUC7) which are located on different chromosomes.

The term "SUC gene" as used herein is used indiscriminately to denote the genes SUC1, SUC2, SUC3, SUC4, SUC5 or SUC7.

In a preferred embodiment, the low invertase activity is obtained by inactivating at least one copy of a SUC gene.

The genome of a strain of *Saccharomyces cerevisiae* may contain zero, one or more copies of each of the genes SUC1, SUC2, SUC3, SUC4, SUC5 and SUC7.

Thus, the present invention provides a broad spectrum strain of *Saccharomyces cerevisiae*, characterized in that:
n copies of a SUC gene are inactivated, n being a whole number, such that the invertase activity of said strain is 20 units or less; and
the maltase activity of said strain, before inactivation of the n copies of the SUC gene, is low.

In particular, the present invention pertains to a broad spectrum strain of *Saccharomyces cerevisiae*, characterized in that:
n copies of a SUC gene are inactivated, n being a whole number, such that the invertase activity of said strain is 20 units or less; and
the maltase activity of said strain, before inactivation of the n copies of the SUC gene, is less than 80 units.

A copy of a SUC gene is inactivated when it is not translated into invertase at all or when it is not translated into a functional invertase.

A functional invertase is an invertase that is capable of converting saccharose into glucose and fructose.

The expression "n inactivated copies of a SUC gene" means that the sum of the number of inactivated copies of the SUC1 gene, the SUC2 gene, the SUC3 gene, the SUC4 gene, the SUC5 gene and the SUC7 gene is equal to n.

The number n of copies of an inactivated SUC gene is necessarily less than or equal to the number of copies of the SUC gene present in the strain.

The term "number of copies of the SUC gene" present in the strain refers to the sum of the number of copies of the SUC1 gene, the SUC2 gene, the SUC3 gene, the SUC4 gene, the SUC5 gene and the SUC7 gene.

The number n of inactivated copies of the SUC gene must therefore be sufficient to obtain an invertase activity of 20 units or less.

In particular, the present invention pertains to a strain as defined above, characterized in that n is 2 or more, preferably 4 or more, more preferably 8 or more.

Preferred strains of the invention have at least 10 inactivated copies of the SUC gene or even at least 12 inactivated copies of the SUC gene.

When a yeast strain has a null or near-null invertase activity, its use may cause problems with coloration of the bread during baking.

The present invention also preferably pertains to a broad spectrum yeast strain as defined above, characterized in that the invertase activity of said strain is 2 units or more.

The n copies of the SUC gene may be inactivated by any means.

Each of the n inactivated copies of the SUC gene may be inactivated by any one of a variety of different means.

The n copies of the SUC gene may, for example, be inactivated by inactivating the transcription of at least one copy of a SUC gene, deletion of at least one copy of a SUC gene, insertion of at least one sequence into at least one copy of a SUC gene, disruption of at least one copy of a SUC gene and/or a mutation in at least one copy of a SUC gene.

Inactivation of transcription of a copy of a SUC gene is, for example, obtained by eliminating the promoter sequence for said SUC gene.

"Deletion" of a copy of a SUC gene means total or partial deletion of the portion coding for a copy of a SUC gene, possibly accompanied by total or partial deletion of the promoter sequence and/or of the terminal sequence.

The expression "coding portion of a gene" is synonymous with "Open Reading Frame" or ORF.

The open reading frame commences with a start codon and terminates with a stop codon.

Insertion of at least one sequence into a copy of a SUC gene means that at least one DNA sequence is inserted into the coding portion of the copy of the SUC gene.

The inserted DNA sequence comprises at least 1 base pair.

In a preferred embodiment, insertion of at least one DNA sequence into a copy of a SUC gene introduces a shift in the reading frame. The shift in the reading frame thus prevents correct translation of the copy of the SUC gene.

Several DNA sequences may be inserted into the coding portion of a copy of a suc gene.

Disruption of a copy of a SUC gene means partial or total deletion of the coding portion of a SUC gene, accompanied by insertion of at least one DNA sequence into the coding portion of a copy of a SUC gene.

During disruption of a copy of a SUC gene, the inserted DNA sequence comprises at least 1 base pair, preferably at least 30 base pairs.

Disruption of a copy of a SUC gene leads to the insertion of a 103 base pair DNA sequence, for example.

Preferably, the copy of the SUC gene inactivated by disruption presents a deletion of at least 1% of the open reading frame of the SUC gene, preferably at least 10%, more preferably at least 20%, still more preferably at least 50%.

The copy of the SUC gene inactivated by disruption may also have a deletion of at least 60% of the open reading frame of the SUC gene or at least 70% of the open reading frame of the SUC gene.

A broad spectrum yeast strain of the invention may comprise copies of the SUC gene inactivated by disruption having different percentage of deletion of the open reading frame of the SUC gene.

The mutation in a copy of a SUC gene is preferably a mutation that introduces a stop codon into the coding region or a mutation that modifies at least one amino acid of the active site of the invertase.

In an advantageous embodiment, when inactivation of the SUC gene is obtained by disruption or insertion, this inactivation does not result in expression of a peptide, a polypeptide or a chimeric protein.

The term "peptide, polypeptide or chimeric protein" means a peptide, polypeptide or chimeric protein that does not exist in the wild type *Saccharomyces cerevisiae* strain and that is obtained by transcription then translation of a sequence portion deriving from the strain and a portion or all of the inserted DNA sequence.

In particular, the present invention pertains to a strain as defined above, characterized in that at least one copy of a SUC gene is inactivated by disruption.

A preferred strain of the invention is characterized in that at least 8 copies, preferably at least 10 copies, of the SUC gene are inactivated by disruption.

Preferred strains of the invention have 10, 11 or 12 copies of the SUC gene inactivated by disruption.

The broad spectrum strains of the invention are generally obtained by inactivation of a large number of copies of the SUC gene.

As indicated below, the Inventors have developed an original method that can be used to rapidly, efficiently and easily carry out multicopy disruption of the SUC gene.

When a broad spectrum strain is obtained by the method of the invention using the cre-lox technique, at least one exogenous DNA sequence remains in the strain.

Thus, the present invention pertains to a strain as defined above, characterized in that it comprises at least one exogenous DNA sequence.

An exogenous DNA sequence corresponds to a DNA sequence that is not present in the genome of a strain of Saccharomyces cerevisiae that has not been genetically modified.

The exogenous DNA sequence preferably derives from inactivation of a copy of a SUC gene by disruption or insertion.

In a preferred embodiment of the invention, the exogenous DNA sequence does not comprise an antibiotic resistance gene.

In a preferred embodiment of the invention, the exogenous DNA sequence is not a coding sequence.

In addition, the exogenous DNA sequence is preferably not translated, whether completely or partially, into a peptide, polypeptide or chimeric protein.

In a preferred embodiment, the exogenous DNA sequence comprises a lox sequence.

A preferred lox sequence of the invention is the following 34 base pair loxP sequence:

(SEQ ID NO: 1)
ATAACTTCGTATAATGTATGCTATACGAAGTTAT.

A preferred exogenous DNA sequence is the following 103 base pair sequence:

(SEQ ID NO: 2)
TGAAGCTTCGTACGCTGCAGGTCGACAACCCTTAATATAACTTCGT

ATAATGTATGCTATACGAAGTTATTAGGTGATATCAGATCCACTAG

TGGCCTATGCG.

SEQ ID No: 2 comprises the loxP sequence of SEQ ID No: 1 (shown in bold characters) and flanking regions.

In particular, a broad spectrum yeast strain of the invention comprises the same number of exogenous sequences as the number of copies of the SUC gene inactivated by disruption.

A broad spectrum yeast strain of the invention in particular comprises the same number of exogenous sequences SEQ ID No: 2 as the number of copies of the SUC gene inactivated by disruption.

More particularly, the present invention pertains to a strain as defined above, selected from the strain deposited at the CNCM under number I-4339, the strain deposited at the CNCM under number I-4340 and the strain deposited at the CNCM under number I-4338.

The strains I-4339, I-4340 and I-4338 were deposited according to the Budapest Treaty on Jul. 8, 2010 at the CNCM (*Collection Nationale de Cultures de Microorganismes*; [National Microorganism Culture Collection]), 25 rue du Docteur Roux, 75724 Paris cedex 15, France.

The broad spectrum *Saccharomyces cerevisiae* strain deposited at the CNCM under number I-4339 is characterized in that:
  10 copies of a SUC gene are inactivated by disruption, its invertase activity being 15 units or less; and
  the maltase activity of said strain before inactivation of the n copies of the SUC gene is less than 70 units.

The broad spectrum *Saccharomyces cerevisiae* strain deposited at the CNCM under number I-4339 comprises 10 sequences SEQ ID No: 2 at the position of the ten copies of the SUC gene inactivated by disruption.

The broad spectrum *Saccharomyces cerevisiae* strain deposited at the CNCM under number I-4340 is characterized in that:
  11 copies of a SUC gene are inactivated by disruption, its invertase activity being 15 units or less; and
  the maltase activity of said strain before inactivation of the n copies of the SUC gene is less than 70 units.

The broad spectrum *Saccharomyces cerevisiae* strain deposited at the CNCM under number I-4340 comprises 11 sequences SEQ ID No: 2 at the position of the eleven copies of the SUC gene inactivated by disruption.

The broad spectrum *Saccharomyces cerevisiae* strain deposited at the CNCM under number I-4338 is characterized in that:
  12 copies of a SUC gene are inactivated by disruption, its invertase activity being 15 units or less; and
  the maltase activity of said strain before inactivation of the n copies of the SUC gene is less than 70 units.

The broad spectrum *Saccharomyces cerevisiae* strain deposited at the CNCM under number I-4338 comprises 12 sequences SEQ ID No: 2 at the position of the twelve copies of the SUC gene inactivated by disruption.

The broad spectrum *Saccharomyces cerevisiae* strains deposited at the CNCM under numbers I-4339, I-4340 and I-4338 do not comprise any exogenous sequences other than the SEQ ID No: 2 sequences.

In particular, the broad spectrum *Saccharomyces cerevisiae* strains deposited at the CNCM with numbers I-4339, I-4340 and I-4338 do not comprise an antibiotic resistance gene.

The broad spectrum yeast strains of the invention, in particular the strains deposited at the CNCM with numbers I-4339, I-4340 and I-4338, were obtained using an original method that is simultaneously rapid, efficient and simple to implement.

Thus, the present invention concerns a method for obtaining a broad spectrum strain of *Saccharomyces cerevisiae*, comprising the steps of:
  selecting a strain of *Saccharomyces cerevisiae* having:
    a maltase activity of less than 80 units; and
    a fermentative capacity of 110 mL or more in an unsweetened dough;
  inactivating m copies of a SUC gene of said selected strain, m being a whole number, such that the invertase activity of the selected and inactivated strain is 20 units or less.

The maltase activity, invertase activity and the fermentative capacity are as defined above.

The selection step preferably comprises selection of a strain of *Saccharomyces cerevisiae* having a fermentative capacity of 120 mL or more in an unsweetened dough, more preferably 130 mL or more in an unsweetened dough.

The expression "m inactivated copies of a SUC gene" means that the sum of the number of inactivated copies of the SUC1 gene, the SUC2 gene, the SUC3 gene, the SUC4 gene, the SUC5 gene and the SUC7 gene is equal to m.

The number m of inactivated copies of a SUC gene is necessarily less than or equal to the number of copies of the SUC gene present in the strain.

The term "number of copies of the SUC gene" present in the strain means the sum of the number of copies of the SUC1 gene, the SUC2 gene, the SUC3 gene, the SUC4 gene, the SUC5 gene and the SUC7 gene.

The number m of inactivated copies of the SUC gene must therefore be sufficient to obtain an invertase activity of 20 units or less.

Thus, the method of the invention can be used to obtain broad spectrum yeast strains as defined above, i.e. yeast strains having:

a fermentative capacity of 110 mL or more in an unsweetened dough; and a fermentative capacity of 90 mL of more in a sweet dough.

In particular, the present invention provides a method as defined above, characterized in that the step of inactivation of m copies of a SUC gene comprises inactivation of the transcription of at least one copy of a SUC gene, deletion of at least one copy of a SUC gene, insertion of at least one sequence into at least one copy of a SUC gene, disruption of at least one copy of a SUC gene and/or a mutation in at least one copy of a SUC gene.

The various means for inactivating a copy of a SUC gene are as defined above. The broad spectrum yeast strains of the invention are preferably industrial yeast strains.

The industrial yeast strains are generally polyploid or even aneuploid.

Regarding the SUC gene, an industrial strain may, for example, comprise at least 12 copies of a SUC gene.

Inactivation of a relatively high number of copies of the SUC gene may thus be necessary in order to obtain an invertase activity of less than 20 units.

In particular, the present invention provides a method as defined above, characterized in that m is 2 or more, preferably 4 or more, more preferably 8 or more.

As an example, the present invention provides a method as defined above, characterized in that m is 10 or more. As an example, m is equal to 10, 11 or 12.

In a preferred embodiment of the invention, at least 4 copies of the SUC gene are inactivated by disruption, preferably at least 8 copies of the SUC gene, more preferably at least 10 copies of the SUC gene. As an example, 10, 11, or 12 copies of the SUC gene are inactivated by disruption.

The aim of the invention is to provide a method that is rapid, efficient and simple to implement for obtaining broad spectrum yeast strains irrespective of the number of copies of the SUC gene to be inactivated by disruption.

However, genetic variability is known to exist between the various members of the family of SUC genes, in the sequences adjacent to the coding portion of the gene (Carlson et al., 1985, Mol. Cell. Biol. 5, 2894-2902).

In addition, if the sequences upstream and downstream of the SUC genes are to be used to inactivate several copies of the SUC gene, it is necessary to construct specific disruption cassettes for each of the 6 members of the family of SUC genes and to use at least 6 sets of homologous recombination sequences.

In order to avoid the method necessitating the construction of a plurality of disruption cassettes, the Inventors have decided to select homologous DNA sequences in the coding portion of the SUC gene.

However, the Inventors have unexpectedly identified a genetic variability in the coding sequence for the members of the family of SUC genes between different strains of *Saccharomyces cerevisiae*.

For example, sequence SEQ ID No: 3 corresponding to the coding portion of the SUC gene with reference YIL162W has 92% identity with the sequence of the coding portion of a SUC gene of the strain deposited at the CNCM under number 1-3399 on Feb. 24, 2005.

However, surprisingly and unexpectedly, the method of the invention can be used to employ the same set of homologous recombination sequences in order to inactivate, by disruption, various copies of the SUC gene, independently of the strain of *Saccharomyces cerevisiae* used.

Thus, the present invention provides a method as defined above, characterized in that the inactivation step comprises:

a step a) of transforming said selected strain with a disruption cassette comprising a selection marker;

a step b) of selecting transformed strains that have integrated the disruption cassette;

an optional step c) of eliminating the selection marker.

The disruption cassette comprises a selection marker, as well as promoter and terminating sequences allowing it to be expressed.

The skilled person knows which selection markers are suitable for use in yeast.

The selection marker is preferably an antibiotic resistance gene.

For example, the selection marker is selected from the kanamycin, blasticidin, phleomycin, hygromycin and nourseothricin resistance gene.

The disruption cassette comprises two homologous recombination sequences that flank the selection marker.

In this case, a homologous recombination sequence is a homologous sequence from a sequence for the coding portion of the copy of the SUC gene or a sequence adjacent to the coding portion of the SUC gene.

Preferably, the homologous recombination sequence is homologous with a sequence for the coding portion of the copy of the SUC gene.

A homologous recombination sequence comprises, for example, in the range 40 to 60 base pairs, preferably in the range of 45 to 55 base pairs.

As an example, a homologous recombination sequence is selected from:

the sequence located from base 1 to base 51 of SEQ ID No: 3;

the sequence located from base 1549 to base 1599 of SEQ ID No: 3;

the sequence located from base 54 to base 104 of SEQ ID No: 3;

the sequence located from base 1497 to base 1547 of SEQ ID No: 3;

the sequence located from base 110 to base 159 of SEQ ID No: 3; and the sequence located from base 1442 to base 1491 of SEQ ID No: 3.

Step b) of selecting transformed strains that have integrated the disruption cassette is carried out by selecting the strains on the basis of the selection marker.

When the selection marker is an antibiotic resistance gene, step b) is carried out by selecting the strains that are capable of multiplying on a medium containing the antibiotic. Only those transformed strains that have integrated the disruption cassette containing the gene for resistance to that antibiotic are capable of multiplication on the medium containing the antibiotic.

The method of the invention preferably comprises a step c) of eliminating the selection marker.

Step c) of eliminating the selection marker may be carried out by spontaneous excision in the yeast.

In order to encourage spontaneous excision, the selection marker is preferably placed between two direct repeat sequences (DRS).

Step c) of eliminating the selection marker is preferably carried out in a directed manner using techniques that are well known to the skilled person.

As an example, the elimination step is carried out with the cre-lox technique. In this case, the disruption cassette comprises two lox sequences flanking the selection marker. The selection marker is then eliminated using the recombinase Cre.

Thus, in particular, the present invention provides a method as defined above, characterized in that the disruption cassette comprises a selection marker flanked by two lox sequences, said lox sequences being flanked by two homologous recombination sequences.

As an example, the lox sequence is the loxP sequence with sequence SEQ ID No: 1.

When more than one copy of the SUC gene has to be inactivated by disruption, it is advantageous to use different disruption cassettes in order to reduce the duration of the inactivation step.

The disruption cassettes may differ one from another in the nature of the selection marker and/or the homologous recombination sequences.

For example, the use of disruption cassettes with one or two homologous recombination sequences that differ one from another can be used to prevent the disruption from being reproduced in a copy that has already been inactivated by disruption.

Moreover, the use of disruption cassettes with different selection markers means that the transformation and selection steps can be carried out in a sequential manner with the various cassettes, then the various markers can be eliminated in a single step.

Thus, the method of the invention can be used to reduce the duration of the inactivation step.

Thus, the present invention pertains to a method as defined above, characterized in that it comprises the following series of steps carried out at least once:
  at least two repetitions of the transformation step a) followed by the selection step b); and
  a step c) of eliminating the selection markers.

In another advantageous embodiment, the present invention pertains to a method as defined above, characterized in that each transformation step a) is carried out with a disruption cassette comprising a different selection marker and/or at least one different homologous recombination sequence.

In particular, the present invention provides a method as defined above, characterized in that it comprises carrying out said series of steps three times and in that at least two series comprise four repetitions of the transformation step a) followed by the selection step b)

In a preferred embodiment, the present invention provides a method for obtaining a broad spectrum strain of *Saccharomyces cerevisiae*, comprising the following steps:
  selecting a strain of *Saccharomyces cerevisiae* having:
    a maltase activity of less than 80 units; and
    a fermentative capacity of 110 mL or more in an unsweetened dough;
  inactivating m copies of a SUC gene of said selected strain, m being a whole number, such that the invertase activity of the selected and inactivated strain is 20 units or less; the inactivation step comprising carrying out the following series of steps at least twice:
    four repetitions of step a) of transformation of said selected strain with at least one disruption cassette comprising a selection marker, followed by step b) of selecting transformed strains that have integrated said disruption cassette; and
    a step c) of eliminating the selection markers;
  and comprising carrying out the following series of steps once:
    at least two repetitions of step a) of transformation with at least one disruption cassette comprising a selection marker, followed by step b) of selecting transformed strains that have integrated said disruption cassette; and
    a step c) of eliminating the selection markers.

The disruption cassettes of each series preferably comprise the same homologous recombination sequences and different selection markers.

The disruption cassettes of the various series preferably comprise one or both different homologous recombination sequences.

For example, the method of the invention requires constructing 4 plasmids each comprising a different selection marker.

Twelve disruption cassettes may then be obtained simply, using only three sets of different primers that comprise the homologous recombination sequences.

The present invention also pertains to a broad spectrum *Saccharomyces cerevisiae* strain that is susceptible of being obtained or is obtained by the method as defined above.

The present invention also pertains to any of the strains derived from the broad spectrum yeast strains of the invention and that share the same properties.

The expression "derived strain" refers to a strain derived by any transformation of any type such as, for example, one or more crossings and/or one or more mutations and/or one or more genetic transformations.

A strain derived by crossing may be obtained by crossing a strain of the invention with the same strain or another strain of the invention, or yet any other strain.

A strain derived by mutation may be a strain that has undergone at least one spontaneous mutation in its genome or at least one induced mutation, for example induced by mutagenesis. The mutation or mutations of the derived strain may or may not be silent.

The expression "mutagenesis" means both conventional mutagenesis obtained by radiation or by mutagenic chemical agents, and insertional mutagenesis by transposition or by integration of an exogenous DNA fragment.

Mutagenesis by radiation includes using UV, X or gamma radiation. Examples of mutagenic chemical agents are EMS (ethyl-methyl sulfonate), EES (ethyl-ethyl sulfonate), nitrosoguanidine, nitrous acid, aflatoxin B1, hydroxylamine, 5-bromouracil, 2-aminopurine, proflavine and/or acridine orange.

A strain derived by genetic transformation is a strain into which an exogenous DNA has been introduced.

Said exogenous DNA may be supplied by means of a plasmid.

Said exogenous DNA is preferably integrated into the genome of the yeast.

Thus, the present invention provides a yeast strain derived from a strain as defined above, characterized in that said derived strain is a broad spectrum strain with an invertase activity of 20 units or less.

The invention also pertains to a method for transforming a broad spectrum yeast strain of the invention, in order to obtain a derived strain as defined above, said transformation method comprising a step of transforming said strain by at least one crossing and/or at least one mutation and/or at least one genetic transformation.

The present invention also concerns yeast strains that are susceptible of being obtained by the transformation method as defined above.

In particular, the present invention pertains to a yeast obtained by culture of a yeast strain as defined above or by culture of a derived yeast strain as defined above.

The yeasts are produced from broad spectrum yeast strains in accordance with the invention, in particular as described in the reference book "Yeast Technology", $2^{nd}$ edition, 1991, G. Reed and T. W. Nagodawithana, published by Van Nostrand Reinhold, ISBN 0-442-31892-8.

Multiplication of yeasts on an industrial scale generally comprises at least the first two steps of the following series of steps:
- multiplying of yeast strain in several stages, initially by semi-anaerobiosis then by aerobiosis;
- separating the yeast produced from its culture medium by centrifugation, in order to obtain a liquid cream yeast containing approximately 12% to 25% dry matter or even a higher dry matter content if the cream yeast is mixed with osmolyte products;
- filtering, in general on a rotary vacuum filter, the liquid cream yeast thus obtained in order to obtain a dehydrated fresh yeast containing 26% to 35% dry matter;
- mixing said fresh dehydrated yeast in order to obtain a homologous mass; extruding the yeast obtained in order to obtain:
  - pressed yeast in the form of fresh yeast blocks or crumbed fresh yeast containing approximately 30% dry matter; or
  - a yeast in the form of particles, in general granules, if the yeast is intended to be dried;
- optionally, drying the particles of yeasts obtained by extrusion in a controlled manner in a stream of hot air, for example by fluidization, in order to obtain dry yeast.

The drying step is preferably rapid drying carried out in the presence of an emulsifying agent.

Emulsifying agents that may be selected for use during the drying step include sorbitan monostearate used, for example, in a concentration of approximately 1.0% (by weight, with respect to the weight of dry yeast).

The yeasts of the invention may be used in any possible form.

As an example, the present invention provides a yeast as defined above, characterized in that it is in the form of a cream yeast, pressed yeast, dry yeast or frozen yeast.

Fresh yeasts are characterized by a high water content compared with dry yeasts. "Fresh yeasts" encompasses cream yeasts and pressed yeasts.

Cream yeasts, also known as "liquid yeasts", are aqueous suspensions of yeast cells with a creamy viscosity.

The term "cream yeast" means a liquid suspension, typically an aqueous suspension, of live yeast cells, said suspension having a dry matter content of at least 12% by weight, generally in the range from approximately 12% to approximately 50% by weight (extended definition of cream yeast).

Preferably, the cream yeast complies with the definition in the strict sense, i.e. it has a dry matter content in the range from approximately 12% to approximately 25% by weight, preferably from approximately 14% to approximately 22% by weight.

Pressed yeasts include yeasts pressed into a compact block, also termed "yeast blocks", which are characterized by a dry matter content in the range from approximately 26% to approximately 35%, and yeasts pressed into granules that are characterized by a water content in the range from approximately 21% to approximately 35%.

Dry yeasts are characterized by a dry matter content of more than approximately 92%.

Frozen yeasts are characterized by a dry matter content in the range from approximately 74% to approximately 80%.

The yeasts of the invention obtained from the culture of broad spectrum yeast strains are effective on unsweetened dough and sweet dough, in particular sweet dough containing a high percentage of saccharose.

The yeasts of the invention are thus used as a fermentation agent for the manufacture of bakery products obtained from unsweetened dough or sweet dough. The performance of a yeast can be evaluated in the bakery by measuring the proof time.

The proof time is defined as the time necessary for a bakery dough to reach a certain height in the mold corresponding to the development of the dough that is desired so that it can be placed in an oven.

The yeasts produced from the various broad spectrum yeast strains of the invention can be used to obtain a proof time comparable to a reference strain for normal dough and to a reference strain for sweet dough (cf. Example 2).

For example, the yeasts obtained from the broad spectrum yeast strains of the invention provide values of proof time that are between the proof time values obtained, on a sweet dough, with two strains suitable for a reference sweet dough (cf. Example 2) and baked using a direct model with 25% saccharose.

The present invention thus also pertains to the use of a yeast as defined above for the manufacture of bakery products.

The yeasts obtained by culture of the broad spectrum strains of the invention may be used in bakery methods of the direct type ("NO-TIME DOUGH") and of the indirect type model ("SPONGE and DOUGH") in unsweetened or sweet dough, with or without mold inhibitor. However, their use is not limited to the specific applications described above and below.

In practice, a direct model does not include a first fermentation between an intensive kneading and dividing of the dough, the dough pieces obtained being fermented in a mold between 35° C. and 40° C., then baked.

A "SPONGE and DOUGH" model is a bakery method comprising two fermentation steps:
- a first step, termed "SPONGE", which corresponds to fermentation of a dough comprising 50% to 70% of the total flour employed, a portion of the water and all of the yeast, for several hours, in general for approximately four hours;
- a second step, termed the "DOUGH" step, in which the SPONGE obtained after the above fermentation is combined with the rest of the flour, the rest of the water and the other ingredients of the dough, the mixture which is thus constituted is kneaded, divided, placed in a mold and fermented then baked; this second in-mold fermentation corresponds to proving and its duration is the proof time.

The percentages are expressed as baker's percentages, the baker's percentage being a method of calculation applied to the ratios of ingredients in which the total weight of the flour always represents 100% and the weight of the other ingredients of the dough is calculated with respect to this weight of flour.

The invention also pertains to a baker's dough containing a yeast in accordance with the invention.

The baker's dough may be an unsweetened dough, a slightly sweet dough or a sweet dough, the sugar preferably being added in the form of saccharose.

The expression "slightly sweet dough" denotes dough with an added sugar content of less than 14% by weight with respect to the weight of flour, preferably 12% or less by weight with respect to the weight of flour.

The invention also proposes a method for preparing a baker's dough, comprising a step for fermentation with a yeast in accordance with the invention.

The invention also provides a method of preparing a baked bakery product, comprising a step for baking a baker's dough as defined above.

Finally, the invention provides a bakery product that can be obtained by the method as defined above.

Thus, by adjusting only the invertase activity parameter, the Inventors obtained broad spectrum yeast strains.

The present invention also pertains to the use of a reduction in invertase activity for obtaining a broad spectrum *Saccharomyces cerevisiae* strain starting from a *Saccharomyces cerevisiae* strain having a low maltase activity and a fermentative capacity of 110 mL or more in an unsweetened dough.

The following examples illustrate the invention without limiting it.

In particular, the examples describe the production of broad spectrum yeast strains according to the invention, and evaluation of the yeasts obtained from these strains by bread making.

EXAMPLES

Example 1: Obtaining Broad Spectrum Yeast Strains According to the Invention

Method and Apparatus
(i) Culture on Molasses Plate

A pre-culture of the yeast strain was produced by seeding 0.3 mg of yeast strain onto a 90 mm diameter Petri dish containing 20 mL of YEG medium (2% glucose). The YEG medium contained 20 g/L of glucose, 5 g/L of yeast extract and 30 g/L of agar. After incubating for 16 hours at 30° C., the yeast cells contained on the Petri dish were harvested.

The yeast cells harvested following pre-culture were seeded onto 140 mm diameter Petri dishes containing molasses, in an amount of 2 mg of dry yeast matter per dish. The "molasses" medium contained 5 g/L of molasses, 0.5 g of $(NH_4)_2HPO_4$, 12.7 g/L of $K_2SO_4$, 5.8 g/L of $Na_2SO_4$, and 30 g/L of agar, at a pH of 5-5.5. After incubating for 20 h at 30° C., the yeast cells contained in the Petri dishes were harvested and washed. The yeast cells were taken up into suspension in 20 mL of demineralized water.

(ii) Disruption of Multiple Copies of SUC Gene
Starting Strain

Disruption of several copies of the SUC gene was carried out on a strain of *Saccharomyces cerevisiae* selected using the following criteria:
a maltase activity of less than 80 units; and
a fermentative capacity of 110 mL or more in an unsweetened dough.

The strain that was selected was then termed the "starting strain".

The starting strain was the strain deposited at the CNCM on Feb. 24, 2005 under number I-3399.

The selected starting strain had a fermentative capacity of more than 130 mL in an unsweetened dough and a maltase activity of less than 70 units (see Table 2).

The number of copies of the SUC gene present in this starting strain was determined to be at least 12 copies by quantitative PCR.

Construction of Disruption Cassettes

Because of the high number of copies of the SUC gene present in the starting strain, 3 series of disruption cassettes were constructed, each series having identical homologous recombination sequences.

Further, each series comprised 4 disruption cassettes that differed in the nature of the selection marker used (kanamycin, blastycidin, phleomycin and hygromycin).

The homologous recombination sequences used were as follows:
for the first disruption series:
the sequence located from base 1 to base 51 of sequence SEQ ID No: 3; and
the sequence located from base 1549 to base 1599 of sequence SEQ ID No: 3;
for the second disruption series:
the sequence located from base 54 to base 104 of SEQ ID No: 3;
the sequence located from base 1497 to base 1547 of SEQ ID No: 3;
for the third disruption series:
the sequence located from base 110 to base 159 of SEQ ID No: 3; and
the sequence located from base 1442 to base 1491 of SEQ ID No: 3.

The primers used to construct the disruption cassettes of each series thus comprised:
one of the above homologous recombination sequences; and
a twenty-base sequence of bases allowing hybridization either side of a region comprising loxP sequences flanking the resistance gene (kanamycin, phleomycin, hygromycin or blastycidin) from the following plasmids: pUG6, pUG66, pUG-hygro, pUG-blast.

The plasmid pUG6 in fact comprises the kanamycin resistance gene, the plasmid pUG66 comprises the phleomycin resistance gene, the plasmid pUG-hygro comprises the hygromycin resistance gene and the plasmid pUG-blast comprises the blastycidin resistance gene.

The disruption cassette was constructed by carrying out a PCR amplification with the primer pair of each series on each of the plasmids pUG6, pUG66, pUG-hygro, pUG-blast.

PCR amplification to construct the series of disruption cassettes was carried out using the enzyme DyNAzyme® (Finnzyme), following the manufacturer's recommendations and using the following temperature cycles: 94° C. for 5 min, 94° C. for 30 s, 55° C. for 30 s, 72° C. for 1 min 30 (these last three steps being repeated so as to carry out 25 cycles), and finally a final elongation cycle at 72° C. for 10 min.

The amplified cassettes were individually purified on a column (nucleo spin extract II kit) and assayed after elution on a Nanodrop apparatus.

Disruption

The yeasts were transformed with the disruption cassette selected using the lithium acetate method (Schiestl and Gietz, 1989).

The transformants were selected on a dish of YEG medium (20 g/L of glucose, 5 g/L of yeast extract, 30 g/L of agar) containing an appropriate concentration of antibiotic as a function of the resistance gene used as a selection marker.

Elimination of Selection Markers

The transformants were transformed with a plasmid comprising the nourseothricin resistance gene and the recombinase gene Cre, using the lithium acetate method (Schiestl and Gietz, 1989).

Transformant clones which had become resistant to nourseothricin were selected and cultivated overnight in the presence of a YEG medium containing 20 g/L of galactose in order to induce expression of the recombinase Cre present on the plasmid.

10 µl of this culture was seeded in a fresh YEG medium. After culturing for 24 h under non-selective conditions in order to encourage loss of plasmid, it was spread onto a YEG gel dish. One hundred clones were analyzed in order to verify the effective loss of resistance to the 4 antibiotic markers of the disruption cassettes (kanamycin, phleomycin, hygromycin and blasticydin) and of the nourseothricin resistance provided by the plasmid comprising the recombinase.

The clones that had lost all resistance to these antibiotics were analyzed in order to verify that this particular step had not affected the growth and the production yield of the yeasts from the selected clones.

Disruption Model

Three series of disruption were carried out.

During each disruption series, the 4 disruption cassettes were used sequentially: transformation with the first cassette and selection of transformants on the basis of the corresponding selection marker, transformation with the second cassette and selection of transformants on the basis of the corresponding selection marker, transformation with the third cassette and selection of transformants on the basis of the corresponding selection marker, then transformation with the fourth cassette and selection of transformants on the basis of the corresponding selection marker.

The 4 selection markers were then eliminated in a single step, by the action of a recombinase.

At the end of each disruption series, the transformants obtained were analyzed by PCR in order to verify integration of the disruption cassette into a SUC locus.

(iii) Assay of Invertase Activity

The yeast strain was cultivated on molasses plate as indicated in (i) above.

The invertase activity was measured as described in Sumner and Howell (*J Biol Chem,* 1935, 108, 51-54).

A known quantity, of the order of a few tens of milligrams, of dry yeast matter and saccharose in a concentration of 0.1 molar were brought into the presence in buffered medium (acetate buffer, 50 mM and pH 4.7), and all placed in a water bath at 30° C.

After 5 minutes incubation, the saccharose inversion reaction was blocked by adding dinitrosalicylic acid reagent which served to assay the reducing sugars formed by means of a colorimetric reaction, using a spectrophotometer at a wavelength of 540 nm.

The invertase activity was expressed in invertase units, one invertase unit corresponding to 1 µmole of liberated reducing sugar, in this case corresponding to one half-micromole of inverted saccharose in 5 minutes per mg of dry yeast matter, at 30° C. and a pH of 4.7, without plasmolysis of the yeast.

(iv) Assay of Maltase Activity

The maltase activity was measured by assaying the liberation of p-nitrophenol following the action of maltase on a chromogenic substrate, 4-nitrophenyl-α-D-glucopyrannoside, as described in Houghton-Larsen and Anders Brandt, Appl. Environ. Microbiol, 2006, p 7176-7182.

The yeast strain was cultivated on molasses plate as indicated above at (i).

The yeast suspension was centrifuged and the cells were seeded in an amount of 1 mg of dry matter per mL into a YEG medium containing 2% of glucose. After incubating for 4 hours, with stirring, at 30° C., the cells were harvested and a cell suspension with 20 mg of dry yeast matter per mL was prepared. 1 mL of said cell suspension was removed in order to grind the cells. After grinding the cells, the supernatant was recovered in order to assay the maltase activity.

The supernatant obtained was diluted 5 to 400 times for the assay. 1.4 mL of substrate in a concentration of 4 mM in a phosphate buffer at a pH of 6.8 was added to 100 µl of diluted supernatant. After incubating for 10 minutes at 30° C., the reaction was stopped by adding 1 mL of a 10% $Na_2CO_3$ solution. The solution was centrifuged for 5 minutes at 4000 rpm and the absorbance of the supernatant was 400 nm.

The concentration of p-nitrophenol in the supernatant was deduced from the values for the absorbances obtained with a p-nitrophenol range of between 100 and 800 nmole/mL.

The results were then expressed in maltase units, one maltase unit corresponding to 1 nmole of p-nitrophenol liberated per minute and per mg of proteins.

(iv) Measurement of Fermentative Capacities

The fermentative capacity of the yeast strains was measured in an unsweetened dough and a sweet dough.

The yeast strains were cultivated on a molasses plate as indicated above in (i).

The yeasts obtained were taken up into suspension in an amount of 150 mg of dry yeast matter for a measurement in unsweetened dough or 300 mg of dry yeast matter for a measurement in sweet dough, in 15 mL of an aqueous solution containing 27 g/L of NaCl and 4 g/L of $SO_4(NH_4)_2$.

The unsweetened dough contained 20 g of flour and the sweet dough contained 6.5 g of saccharose and 25 g of flour.

In order to form the dough pieces, a mixture of flour (with or without saccharose) and said yeast suspension were mixed in a kneader for 40 seconds in order to obtain a dough that was then placed in a receptacle in a water bath at 30° C. 13 minutes after mixing was started, the receptacle containing the dough was hermetically sealed.

The volume of gas released was measured during the first hour and during the second hour using a Risograph (National Manufacturing, Lincoln, Nebr.). The total volume in mL was then indicated for 2 hours at 30° C.

Results (i) Multi-Copy Disruption of SUC Gene

The two homologous recombination sequences for the first series comprised the ATG start codon and the stop codon of SUC2. After a double homologous recombination event with insertion of the disruption cassette into the targeted locus, 1497 bp of the targeted SUC gene was deleted.

Using the same principle, the disruption cassettes for the second series were used to delete 1392 bp of the SUC gene at the targeted locus.

Since the two homologous recombination sequences of the second series were situated in the region of the SUC gene deleted by using the disruption cassettes of the first series, the double homologous recombination event could only occur at a SUC locus that had not undergone disruption.

In the same manner, the disruption cassettes of the third series could be used to delete 1173 bp of the SUC gene at the targeted locus. Since the two homologous recombination sequences of the third series were situated in the region of the SUC gene deleted by using the disruption cassettes of the second series, the double homologous recombination event could only occur at a SUC locus that had not undergone disruption.

The first series could be used to disrupt 94% of the ORF of a SUC gene, the second series, 87% and the third series, 73%.

Strains having up to 12 copies of the SUC inactivated by disruption were thus obtained. The strains were denoted by the character "Δ" followed by a cipher indicating the number of copies of the SUC gene inactivated by disruption.

The strains tested below were as follows: Δ4, Δ8, Δ9, Δ10, Δ11, Δ12.

(ii) Assay of invertase activity of strains obtained.

The invertase activity of the various strains obtained as well as that of the starting strain were measured as indicated in the Method and Apparatus section.

The invertase activity of the 3 control strains with a broad spectrum activity (T1, T2 and T3) was also measured.

Starting from 8 copies of the SUC gene inactivated by disruption, the invertase activity was reduced by a factor of more than 20 (cf. Table 1a).

The strains that had at least 8 copies of the SUC gene inactivated by disruption had an invertase activity of less than 20 units.

TABLE 1a

| Yeast strain | Invertase activity (in units) |
|---|---|
| Starting strain | 314 |
| Δ4 + marker | 72 |
| Δ8 + marker | 13 |
| Δ9 + marker | 14 |

TABLE 1b

| Yeast strain | Invertase activity (in units) |
|---|---|
| Starting strain | 343 |
| Δ10 + marker | 11 |
| Δ10 | 10 |
| Δ11 + marker | 8 |
| Δ11 | 12 |
| Δ12 + marker | 9 |
| Δ12 | 10 |
| T1 | 27 |
| T2 | 10 |
| T3 | 11 |

Beyond 10 copies of the SUC gene inactivated by disruption, disruption of one or more supplemental copies did not further reduce the invertase activity (cf. Table 1b).

The invertase activity measured on the strains before eliminating the antibiotic markers could be used to demonstrate that the step for eliminating markers had no effect on the invertase activity of the strains (cf. Table 1b).

The control strains T2 and T3 had an invertase activity similar to the various strains obtained. The control strain T1, though, had an invertase activity that was a little higher (cf. Table 1b).

(iii) Assay of Maltase Activity

The maltase activity of the starting strain was much less than 80 units.

TABLE 2

| Yeast strain | Maltase activity (in units) |
|---|---|
| Starting strain | 63 |
| Δ10 | 131 |
| Δ11 | 135 |
| Δ12 | 225 |
| SDS | 36 |
| T1 | 575 |
| T2 | 551 |
| T3 | 542 |

Surprisingly, the maltase activity of strains Δ10, Δ11 and Δ12 of the invention had increased (between 120 and 230 units).

The maltase activity of a strain suitable for a sweet dough (SDS) was 40 units and that of the control broad spectrum strains was more than 500 units.

(iv) Measurement of Fermentative Capacities

The broad spectrum character of the strains obtained was evaluated by measuring the fermentative capacities in an unsweetened dough and in a sweet dough.

The fermentative capacities of the broad spectrum control strains T1 to T3, of the starting strain and of a strain suitable for a sweet dough (SDS) were also evaluated.

The strain suitable for a sweet dough was by definition effective on a sweet dough, but was not suitable for unsweetened dough.

Table 3 indicates the fermentative capacities in an unsweetened dough and Table 4 in a sweet dough.

TABLE 3

| Tested strain | 1st hour | 2nd hour | Total 2 hours |
|---|---|---|---|
| Starting strain | 52 | 85 | 137 |
| SDS | 37 | 58 | 95 |
| Δ10 + marker | 52 | 92 | 144 |
| Δ10 | 52 | 92 | 144 |
| Δ11 + marker | 51 | 92 | 143 |
| Δ11 | 57 | 90 | 147 |
| Δ12 + marker | 47 | 91 | 138 |
| Δ12 | 52 | 94 | 146 |
| T1 | 67 | 87 | 154 |
| T2 | 59 | 85 | 144 |
| T3 | 68 | 88 | 156 |

The strains exhibiting several copies of the SUC gene inactivated by disruption and the starting strain had similar fermentative capacities in an unsweetened dough during the first hour which were much higher than that of the strain suitable for a sweet dough, but lower than the broad spectrum control strains (cf. Table 3).

The fermentative capacity of the strains with several copies of the SUC gene inactivated by disruption during the second hour in an unsweetened dough was higher than that of the starting strain and that of the control broad spectrum strains (cf. Table 3). They were also substantially higher than the fermentative capacity of a strain suitable for a sweet dough.

The fermentative capacity of the strains exhibiting several copies of the SUC gene inactivated by disruption over the totality of 2 hours in an unsweetened dough was slightly higher than the starting strain and substantially higher than the strain suitable for a sweet dough and was at the level of the values obtained for the control broad spectrum strains (cf. Table 3).

The strains exhibiting several copies of the SUC gene inactivated by disruption thus had a fermentative capacity profile in an unsweetened dough which was quite particular, and presented differences both as regards the starting strain, the strain suitable for a sweet dough and the broad spectrum control strains.

TABLE 4

| Tested strain | 1st hour | 2nd hour | Total 2 hours |
|---|---|---|---|
| Starting strain | 15 | 37 | 53 |
| SDS | 45 | 79 | 124 |
| Δ10 | 43 | 84 | 127 |
| Δ11 + marker | 41 | 83 | 124 |
| Δ11 | 45 | 84 | 129 |
| Δ12 + marker | 36 | 74 | 109 |
| Δ12 | 35 | 73 | 108 |
| T1 | 48 | 80 | 127 |
| T2 | 37 | 65 | 103 |
| T3 | 46 | 67 | 113 |

Table 4 indicates the fermentative capacities obtained for a sweet dough.

The fermentative capacity of strains exhibiting several copies of the SUC gene inactivated by disruption, the control broad spectrum strains and the strain suitable for a sweet dough (SDS) was much higher than that of the starting strain.

The strains Δ10, Δ11, the strain suitable for a sweet dough (SDS) and the broad spectrum control strain T1 provided fermentative capacities that were similar in a sweet dough during the first hour, the second hour and the whole of the 2 hours.

The strain Δ12 and the broad spectrum controls T2 and T3 had slightly lower fermentative capacities.

The results obtained show that the yeast strains Δ10, Δ11 and Δ12 were yeast strains according to the invention that had very interesting broad spectrum properties.

The yeast strains Δ10, Δ11 and Δ12 respectively corresponded to the strains deposited at the CNCM under numbers I-4339, I-4340 and I-4338.

Example 2: Evaluation of Yeasts Obtained from Strains of the Invention for Breadmaking Method and Apparatus
(i) Production of Yeasts The yeasts were produced from yeast strains according to the invention in 20 liter fermenters, in semi-continuous mode, as described in the reference book "Yeast Technology", $2^{nd}$ edition, 1991, G. Reed and T. W. Nagodawithana, published by Van Nostrand Reinhold, ISBN 0-442-31892-8.

The yeasts were produced in the form of a liquid yeast and pressed yeast.

(ii) Bread Making Tests

The yeasts obtained were evaluated in an application using a direct model, in a dough containing a high concentration of saccharose (25% of saccharose, as a baker's percentage).

The recipe used is indicated in Table 5 below.

The improver supplied the mixture of oxidizing agents and reducing agents, the enzymes as well as the conventional emulsifying agents meant that the manufacturing process of this direct bread making model could be optimized, quality was good and the bread obtained kept well.

TABLE 5

| Ingredients | Quantities (baker's %) |
|---|---|
| Flour | 100 |
| Water | 46 |
| Raising agent | 6 |
| Fat | 7.5 |
| Improver | 1 |
| Saccharose | 25 |
| Salt | 1.7 |

The following protocol was applied:
1. Weigh the solid ingredients;
2. Measure the ambient temperature and the temperature of the flour;
3. Adjust the temperature of the water in order to obtain a dough temperature of 27° C.±0.5° C.;
4. Place the ingredients in a MacDuffy® bowl of a HobartA200® kneader;
5. Mix the dry ingredients at a first speed for 1 min, then add the fat, water and yeast;
6. Start kneading using the following program:
   at $1^{st}$ speed for 5 min;
   allow to rest for 4 min;
   at $2^{nd}$ speed for 5 min;
7. Obtain a dough at a temperature of 27° C.±0.5° C.;
8. Remove 50 g of dough, roll briefly and place in a Risograph bowl; place said bowl in a water bath at 30° C., connect the bowl up to the measuring apparatus and initiate measurement for 2 hours;
9. Punch down the mass at an ambient temperature of 22° C. for 10 min;
10. Divide into 320 g dough pieces;
11. Shape into ball and cover;
12. Leave to rest for 10 min;
13. Shape the dough;
14. Place the 320 g dough pieces into molds (mold dimensions: base 185×75 mm; top of mold 200×90 mm; height of mold 75 mm);
15. Determine the proof time in a Stericult® incubator at 35° C. and 90% relative humidity, the proof time being the time between placing in the incubator and the time at which the dough has reached a height of 85 mm in the mold;
16. Bake in a REED® swing oven at 180° C. for 21 min;
17. Measure the volume of the loaves after cooling for at least one hour.

The following parameters were evaluated:
the proof time, expressed as a percentage with respect to a reference yeast;
the specific volume of the bread (volume of bread with respect to weight, SV), expressed as a percentage with respect to a reference yeast; and
the gas release (GR) measured using the Risograph at 2 h and at 30° C., starting from a 50 g dough piece, expressed as a percentage with respect to a reference yeast.

Results

The yeasts produced from the yeast strain Δ11 were evaluated in an application containing a large quantity of saccharose (direct model with 25% saccharose).

Table 6 presents the results obtained with yeasts obtained from strain Δ11 of the invention, compared with the starting strain and two strains suitable for a sweet dough (SDS1 and SDS2).

The strain SDS1 was a standard strain taken from strains suitable for a sweet dough and the strain SDS2 was the best strain suitable for a sweet dough from the Applicant.

TABLE 6

| Strain used | Yeast | Proof time (%) | SV (%) | GR (%) |
|---|---|---|---|---|
| Starting strain | Liquid yeast | +20 | −13 | −26 |
| | Pressed yeast | +29 | −20 | −36 |
| Strain Δ11 | Liquid yeast | −13 | +9 | +27 |
| | Pressed yeast | −11 | +9 | +24 |
| SDS1 | Pressed yeast | −1 | +1 | −1 |
| SDS2 | Pressed yeast | −24 | +26 | +47 |

The percentages were calculated with respect to the values obtained with a reference yeast.

As expected, the yeasts obtained from the starting strain were not at all suitable for bread making using a sweet dough.

The yeasts obtained from strain Δ11 of the invention produced values for the proof time, specific volume of the loaf and gas release that were between the values obtained with yeasts obtained from the strain SDS1 and those obtained with yeasts obtained from the strain SDS2.

The yeasts obtained from the strain Δ11 are thus suitable for use in sweet dough.

What is claimed is:

1. A method for obtaining a broad spectrum strain of *Saccharomyces cerevisiae*, comprising the steps of:
   selecting a strain of *Saccharomyces cerevisiae* having:
   an invertase activity of 300 units or more;
   a maltase activity of less than 80 units; and
   a fermentative capacity of 110 mL or more in an unsweetened dough; and
   inactivating m copies of a SUC gene of said selected strain by disruption, m being a whole number equal to 10, 11 or 12, such that the invertase activity of the selected and inactivated strain is 20 units or less, wherein the inactivation step comprises:
   a step a) of transforming said selected strain with a disruption cassette comprising a selection marker flanked by two lox sequences, said lox sequences being flanked by two homologous recombination sequences, wherein each of said two homologous recombination sequences comprises a fragment of SEQ ID NO: 3;
   a step b) of selecting transformed strains that have integrated the disruption cassette; and
   an optional step c) of eliminating the selection marker, wherein the ratio between invertase and maltase is altered from at least 5:1 before inactivation to at least 1:5 after inactivation of the m copies of SUC genes in the *Saccharomyces cerevisiae* strain.

2. The method as claimed in claim 1, wherein the fragment of SEQ ID NO: 3 comprises, or consists of, between 40 and 60 consecutive base pairs of SEQ ID NO: 3.

3. The method as claimed in claim 2, wherein the fragment of SEQ ID NO: 3 is selected from the group consisting of the sequence consisting of the sequence ranging from base 1 to base 51 of SEQ ID NO: 3, the sequence ranging from base 1549 to base 1599 of SEQ ID NO: 3, the sequence ranging from base 54 to base 104 of SEQ ID NO: 3, the sequence 110 to base 159 of SEQ ID NO: 3, and the sequence ranging from base 1442 to base 1491 of SEQ ID NO: 3.

4. The method as claimed in claim 1, wherein each of the lox sequences comprises SEQ ID NO: 1.

5. The method as claimed in claim 1, comprising the following series of steps carried out at least once:
   at least two repetitions of the transformation step a) followed by the selection step b); and
   a step c) of eliminating the selection markers.

6. The method as claimed in claim 5, wherein each transformation step a) is carried out with a disruption cassette comprising a different selection marker and/or at least one different homologous recombination sequence.

7. The method as claimed in claim 5, comprising carrying out said series of steps three times, wherein at least two series comprise four repetitions of the transformation step a) followed by the selection step b).

* * * * *